United States Patent
Nubel

(10) Patent No.: US 10,987,662 B2
(45) Date of Patent: Apr. 27, 2021

(54) DESILICATED ZSM-5 CATALYSTS FOR XYLENE ISOMERIZATION

(71) Applicant: Ineos US Chemicals Company, Naperville, IL (US)

(72) Inventor: Philip Nubel, Naperville, IL (US)

(73) Assignee: Ineos US Chemicals Company, Naperville, IL (US)

( * ) Notice: Subject to any disclaimer, the term of this patent is extended or adjusted under 35 U.S.C. 154(b) by 390 days.

(21) Appl. No.: 15/736,554

(22) PCT Filed: Aug. 11, 2016

(86) PCT No.: PCT/US2016/046589
§ 371 (c)(1),
(2) Date: Dec. 14, 2017

(87) PCT Pub. No.: WO2017/030906
PCT Pub. Date: Feb. 23, 2017

(65) Prior Publication Data
US 2018/0169636 A1    Jun. 21, 2018

Related U.S. Application Data

(60) Provisional application No. 62/206,511, filed on Aug. 18, 2015.

(51) Int. Cl.
| | | |
|---|---|---|
| *B01J 29/04* | (2006.01) | |
| *B01J 29/40* | (2006.01) | |
| *B01J 35/10* | (2006.01) | |
| *C01B 39/02* | (2006.01) | |
| *B01J 29/48* | (2006.01) | |
| *B01J 29/42* | (2006.01) | |
| *C07C 5/27* | (2006.01) | |
| *B01J 35/02* | (2006.01) | |
| *B01J 37/08* | (2006.01) | |
| *C07C 5/22* | (2006.01) | |
| *C07C 15/08* | (2006.01) | |

(52) U.S. Cl.
CPC ............ *B01J 29/405* (2013.01); *B01J 29/40* (2013.01); *B01J 29/42* (2013.01); *B01J 29/48* (2013.01); *B01J 35/023* (2013.01); *B01J 35/109* (2013.01); *B01J 35/1014* (2013.01); *B01J 35/1019* (2013.01); *B01J 35/1057* (2013.01); *B01J 35/1061* (2013.01); *B01J 37/08* (2013.01); *C01B 39/026* (2013.01); *C07C 5/222* (2013.01); *C07C 5/2737* (2013.01); *C07C 5/2775* (2013.01); *C07C 15/08* (2013.01); *B01J 29/041* (2013.01); *B01J 29/042* (2013.01); *B01J 29/045* (2013.01); *B01J 35/108* (2013.01); *B01J 2229/10* (2013.01); *B01J 2229/16* (2013.01); *B01J 2229/20* (2013.01); *B01J 2229/37* (2013.01); *B01J 2229/38* (2013.01); *B01J 2229/40* (2013.01); *C07C 2529/40* (2013.01); *C07C 2529/48* (2013.01); *Y02P 20/52* (2015.11)

(58) Field of Classification Search
CPC ....... Y02P 20/52; C01B 39/026; C01B 39/38; C07C 2529/40
USPC ................ 502/60, 63, 64, 66, 69, 71, 77, 85
See application file for complete search history.

(56) References Cited

U.S. PATENT DOCUMENTS

| | | |
|---|---|---|
| 3,856,871 A | 12/1974 | Haag et al. |
| 5,759,950 A | 6/1998 | Gui et al. |
| 6,184,167 B1 | 2/2001 | Mao et al. |
| 2005/0113619 A1 | 5/2005 | Schmidt et al. |
| 2008/0307697 A1 | 12/2008 | Fieni et al. |

OTHER PUBLICATIONS

Fernandez et al., "Hierarchical ZSM-5 Zeolites in Shape-Selective Xylene Isomerization: Role of Mesoporosity and Acid Site Speciation", Chem. Eur. J. 2010,16, pp. 6224-6233.*
Corma el al., "Designing MFI-based catalysts with improved catalyst life for C3= and C5= oligomerization to high-luality liquid fuels," J. of Catal. 300:183-196 (2013).
Verboekend et al., "Full Compositional Flexibility in the Preparation of Mesoporous MFI Zeolites by Desilication," Journal of Physical Chemistry, vol. 115, No. 29, Jul. 28, 2011, pp. 14193-14203.
Verboekend et al., "Supporting Information" to the above 2011.
Caicedo-Realpe et al., "Mesoporous ZSM-5 Zeolites Prepared by a Two-Step Route Comprising Sodium Aluminate and Acid Treatments," Microporous and Mesoporous Materials, vol. 128, No. 1, Aug. 14, 2009, pp. 91-100.
Heracleous et al., "Microporous/Mesoporous Pt/ZSM-5 Catalysts for iydroisomerization of BTL-Naphtha," Industrial & Engineering Chemistry Research, vol. 52, No. 41, Oct. 16, 2013, pp. 14567-14573.
Hoff, et al., "Tailoring ASM-5 Zeolites for the Fast Pyrolysis of Biomass to Aromatic Hydrocarbons," ChemSusChem, vol. 9, No. 12, pp. 1473-1482, 2016.

(Continued)

*Primary Examiner* — Elizabeth D Wood
(74) *Attorney, Agent, or Firm* — McDonnell Boehnen Hulbert & Berghoff LLP

(57) ABSTRACT

A method of making a xylene isomerization catalyst comprises the steps of (i) contacting a ZSM-5 zeolite starting material having a silica to alumina molar ratio of 20 to 50 and having a mesopore surface area in the range of 50 m²/gram to 200 m²/gram in a reactor with a base to provide an intermediate zeolite material; (ii) recovering the intermediate ZSM-5 zeolite material of step (i); (iii) contacting the intermediate zeolite material with an acid to provide an acid treated ZSM-5 zeolite product; (iv) recovering the acid treated ZSM-5 zeolite material; and (v) calcining the acid treated ZSM-5 zeolite material to provide a desilicated ZSM-5 zeolite product having a silica to alumina molar ratio of 20 to 150 and having a mesopore surface area in the range of 100 m²/gram to 400 m²/gram.

7 Claims, 10 Drawing Sheets

(56) References Cited

OTHER PUBLICATIONS

Fernandez et al., "Hierarchical ASM Zeolites in Shape-Selective Xylene Isomerization: Role of Mesoporosity and Acid Site Speciation," Chemistry—A European Journal, vol. 16, No. 21, Jun. 2010, pp. 6224-6233.

Van Donk, et al., "Generation, Characterization and Impact of Mesopores in Zeolite Catalysts," Catalysis Reviews, vol. 45, No. 2, 2003, pp. 297-319.

* cited by examiner

Catalyst Q

US 10,987,662 B2

DESILICATED ZSM-5 CATALYSTS FOR XYLENE ISOMERIZATION

FIELD OF THE INVENTION

This invention relates to a novel xylene isomerization catalyst and method of making same.

BACKGROUND OF THE INVENTION

Para-xylene (also "p-xylene" or "PX") is an important hydrocarbon feed material for the manufacture of terephthalic acid. Para-xylene is generally considered the most important of $C_8$ aromatic isomers, being used as an intermediate or starting material for such diverse end uses as synthetic fibers and bottle plastic. Para-xylene is typically obtained from a $C_8$ aromatic hydrocarbon mixture derived from reformate by processes including aromatic extraction and fractional distillation. Although the composition of this starting $C_8$ aromatic hydrocarbon mixture varies over a wide range, the mixture generally comprises 5 to 40 wt % ethylbenzene, with the balance, xylenes, being divided between approximately 50 wt % meta-xylene and 25 wt % each of para-xylene and ortho-xylene (this distribution considered the nominal "equilibrium concentration" of xylenes). Since, by some accounts, 80 wt % or more of the end use of xylenes involves the conversion of para-xylene to the above-mentioned end uses, obtaining para-xylene from its $C_8$ isomers meta-xylene, ortho-xylene, and ethylbenzene, is the subject of a vast amount of continuing research.

SUMMARY OF THE INVENTION

What is provided herein is a method of making a xylene isomerization catalyst comprising the steps of (i) contacting a ZSM-5 zeolite starting material having a silica to alumina molar ratio of about 20 to about 50 and having a mesopore surface area in the range of about 50 m²/gram to about 200 m²/gram in a reactor with a base at a temperature of about 20° C. to about 100° C. for a caustic treatment period of about 1 minute to about 10 hours to provide an intermediate zeolite material, wherein the ZSM-5 zeolite is present in the base in an amount of about 1 weight % to about 20 weight %; (ii) recovering the intermediate ZSM-5 zeolite material of step (i); (iii) contacting the intermediate zeolite material with an acid at a temperature of about 20° C. to about 100° C. for an acid treatment period of about 1 minute to about 10 hours to provide to provide an acid treated ZSM-5 zeolite product; (iv) recovering the acid treated ZSM-5 zeolite material; and (v) calcining the acid treated ZSM-5 zeolite material at a temperature in the range of about 300° C. to about 700° C. for a period of time in the range of about 0.2 hours to about 6 hours to provide a desilicated ZSM-5 zeolite product having a silica to alumina molar ratio of about 20 to about 150 and having a mesopore surface area in the range of about 100 m²/gram to about 400 m²/gram.

The ZSM-5 zeolite starting material has an average crystal size length, width and thickness of less than 1 micron.

The base is selected from the group consisting essentially of: NaOH, LiOH, KOH, RbOH, CsOH, Mg(OH)$_2$, Ca(OH)$_2$, NH$_4$OH, Li$_2$O, Na$_2$O, K$_2$O, Rb$_2$O, Cs$_2$O, MgO, and CaO; Alkali metal alkoxides having the formula R'OM wherein R' is selected from the group consisting essentially of methyl, ethyl, propyl, isopropyl, butyl, pentyl, and phenyl, and M is selected from the group consisting essentially of Li, Na, and K; Alkyl ammonium hydroxides having the formula R"NH$_3$OH, R"$_2$NH$_2$OH, R"$_3$NHOH, R"$_4$NOH, wherein R" is selected from the group consisting essentially of methyl, ethyl, propyl, isopropyl, and butyl; or any combination thereof.

In one embodiment, the base is added to the reactor incrementally during the caustic treatment period. In another embodiment, the base is added to the reactor continuously during the caustic treatment period.

The acid is selected from the group consisting essentially of HF, HCl, HBr, HI, HNO2, HNO3, H2SO3, H2SO4, H3PO3, H3PO4, H3BO3, oxalic acid, citric acid, acetic acid, benzoic acid, formic acid, propionic acid, fluoroacetic acid, trofluoroacetic acid, lactic acid, tartaric acid, ascorbic acid, malonic acid, maleic acid, succinic acid, glutaric acid, adipic acid, 2-hydroxybenzoic acid, 3-hydroxybenzoic acid, and 4-hydroxybenzoic acid, or any combination thereof.

What is also provided herein is a desilicated ZSM-5 zeolite product having a silica to alumina molar ratio of about 20 to about 150 and having a mesopore surface area in the range of about 100 m²/gram to about 400 m²/gram.

In one embodiment, the product further comprises a support selected from the group consisting essentially of an alumina support, a silica support, a silica-alumina support, a titania support, and a zirconia support, or any combination thereof. In another embodiment, the product further comprises a support and a hydrogenation metal from the group consisting essentially of molybdenum, platinum, palladium, rhodium, ruthenium, nickel, iron, osmium, iridium, tungsten, and rhenium. In one embodiment, the hydrogenation metal is present in an amount of about 0.5 weight % to about 10 weight %, and preferably from about 1 weight % to about 5 weight %.

BRIEF DESCRIPTION OF THE DRAWINGS

In the following detailed description, reference will be made to the attached drawings in which.

DETAILED DESCRIPTION OF THE INVENTION

Figure 1:
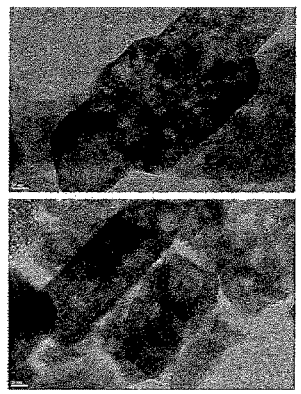
FIG. 1 shows an actual TEM image of a ZSM-5 zeolite powder after desilication.

Turning now to the drawings, and more particularly to FIG. 1, what is shown are actual TEM images of a ZSM-5 zeolite powder after desilication. The small scale bars in the lower left corners represent a length of 10 nm. Mesopore holes and cavities are seen in the desilicated material.

A number of commercial ZSM-5 zeolites before and after desilication treatments were screened using a multi fixed bed reactor catalyst testing instrument. The most active ZSM-5 for xylene isomerization, Catalyst C, was then selected for more detailed studies with the goal of optimizing the desilication process and the performance of the resulting catalysts.

A total of ten commercial ZSM-5 powders with varying Al contents and crystallite sizes with SAR values ($SiO_2/Al_2O_3$ molar ratio) less than 100 were evaluated. Analytical characterization data for these ZSM-5 zeolites are given in Table I along with those of Catalyst C and two desilicated materials prepared from it. The ZSM-5 samples were calcined in air at 510° C. for 4 hours prior to catalytic testing using the following temperature program: dry at 165° C. for 4 hours, ramp to 510° C. over 4 hours, hold at 510° C. for 4 hours, and cool to 50° C.

filtered, washed with DI water, dried, and calcined at 510° C. for 4 hours. The first preparation Catalyst M employed twice the amount of ZSM-5 relative to NaOH (100 g ZSM-5, 1650 g NaOH) to reduce yield losses, followed by a solution of 100 g oxalic acid dihydrate in 1000 mL DI water. The second preparation Catalyst N was made using 60 g ZSM-5 in 1980 g 0.5 M NaOH for desilication and then a solution of 144 g oxalic acid dihydrate in 1440 mL DI water for the subsequent acid treatment.

Catalyst characterization methods employed included inductively coupled plasma spectroscopy (ICP), x-ray fluorescence spectroscopy (XRF), and C—H—N elemental analyses, x-ray diffraction (XRD) for phase identification and percent crystallinity, $N_2$ physisorption for surface area and porosity, scanning electron microscopy (SEM) and transmission electron microscopy (TEM) for crystallite size, morphology, and mesopore structure.

Multi fixed bed reactor catalyst testing instrument runs employed charges of 40 mg (+/−0.2 mg) of Catalyst A ground and sieved to 53-200 microns and loaded in 2.0-mm ID multi fixed bed reactor catalyst testing instrument reactor tubes. Pure ZSM-5 powders were screened to 53-200 microns prior to reactor loading, and charges of 8.0 mg (+/−0.1 mg) were employed in order to have the same loading of molecular sieve as the Catalyst A (20 wt % borosilicate sieve on alumina support) as disclosed in U.S. Pat. No. 6,518,472. The 8.0 mg of each ZSM-5 were loaded into the multi fixed bed reactor catalyst testing instrument reactor tube in between two 20-mg charges of inert alpha-alumina. Each catalyst was usually tested in duplicate (two reactors in the same multi fixed bed reactor catalyst testing instrument run), and in the great majority of cases the results of the duplicate trials were very similar. Results were calculated as averages of the duplicates. Multi fixed bed reactor catalyst testing instrument runs began at isomerization conditions for ~1 day (600° F., 225 psig, 1.5:1 $H_2$/HC molar, with a mixed xylenes feed rate equivalent to 38 h$^{-1}$

TABLE I

Analytical Data

| | ICP | | | | | | $N_2$ Physisorption | | |
|---|---|---|---|---|---|---|---|---|---|
| ZSM-5 Sample | Al (ppm) | Na (ppm) | Fe (ppm) | SAR[a] | Al % calculated from SAR | XRD % Cryst.[b] | Total BET S.A. (m²/g) | External (Mesopore) S.A. (m²/g) | Micropore vol (cc/g) |
| D | 37771 | 684.7 | 176.4 | 19.8 | | 81.8 | | | |
| E | 21621 | 66.62 | 45.78 | 37.0 | | 84.8 | | | |
| F | 34291 | 117.0 | 221.9 | 21.3 | | 86.4 | | | |
| G | 27021 | 407.3 | 206.3 | 27.4 | | 97.6 | | | |
| H | 27651 | 392.4 | 211.1 | 27.5 | | 97.9 | | | |
| I | 19981 | 61.25 | 392.8 | 38.6 | | 97.8 | | | |
| J | 12811 | 417.1 | 126.2 | 60.7 | | 98.5 | | | |
| K | 9079 | 74.64 | 476.6 | 89.1 | | 88.7 | | | |
| L | 9806 | 120.1 | 280.0 | 83.8 | | 92.3 | | | |
| C | 27630 | 103.3 | 96.9 | 28 | 2.9 | 101% | 457 | 103 | 0.144 |
| M | 20617 | 80.1 | 35.1 | 39 | 2.2 | 71% | 544 | 209 | 0.137 |
| N | 12560 | 155.2 | 27.5 | 64 | 1.4 | 58% | 604 | 263 | 0.148 |

[a]$SiO_2/Al_2O_3$ mole ratio calculated from ICP data
[b]relative to a reference ZSM-5

The two desilicated ZSM-5 samples shown at the bottom of Table I were made as follows: Catalyst C was treated with 0.5M aqueous NaOH at 85° C. for 90 minutes, cooled, filtered, washed with deionized ("DI") water, treated with ~10 wt % aqueous oxalic acid for 2 hours at 70° C., cooled, WHSV for 40 mg catalyst) and then switched to ethylbenzene conversion conditions (700° F., 200 psig, 2:1 $H_2$/HC molar, 10 h$^{-1}$ WHSV mixed xylenes feed) for 1-2 days. Later runs were performed with a return to xylene isomerization ("Isom") conditions for a day after completion of ethylbenezene conversion ("EBC") conditions. Some of the final runs were done using an EBC-Isom sequence with no initial Isom conditions period due to significant deactivation that typically was observed during the initial Isom periods. Mixed xylenes comprising 25% orthoxylene, 50% metaxylene, 9.5% paraxylene, and 12% ethylbenzene were employed as the hydrocarbon feed.

All the commercial ZSM-5 samples were tested for performance after calcination, as were two desilicated materials prepared from Catalyst C as described in the Experimental section.

Figure 2:
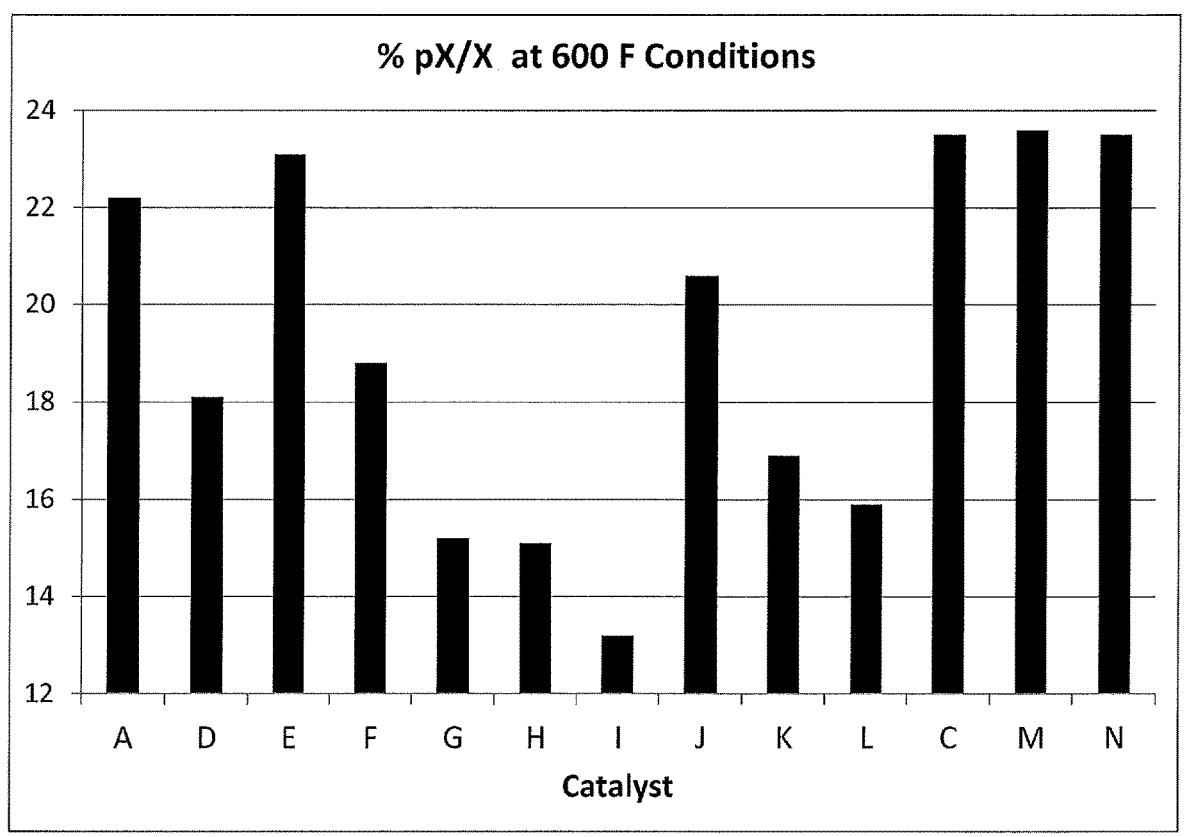
FIG. 2 shows xylene isomerization results for ZSM-5 Zeolites and Desilicated ZSM-5 Zeolites.

The results shown in FIG. 2 are those of two multi fixed bed reactor catalyst testing instrument runs collected from 21-25 hours on stream under the initial Isom conditions, during which each reactor was sampled once. The % pX/xylenes reactor effluent (pX/X) values represent averages of the duplicate tests of each catalyst (except for Catalyst C). All the duplicate pairs were in excellent agreement, with pX/X values that were within 0.1-0.2 absolute % of each other. The Catalyst A reference catalyst yielded 22.2% pX/X in both runs; therefore the isomerization results of both runs were combined in FIG. 2.

The chart in FIG. 2 shows that only two of the ZSM-5 zeolites had greater isomerization activity than Catalyst A, Catalyst C and Catalyst E. Both of these were composed primarily of small crystals well below 1 micron in size, whereas the other zeolites consisted of crystals larger than 1 micron.

Figure 3:
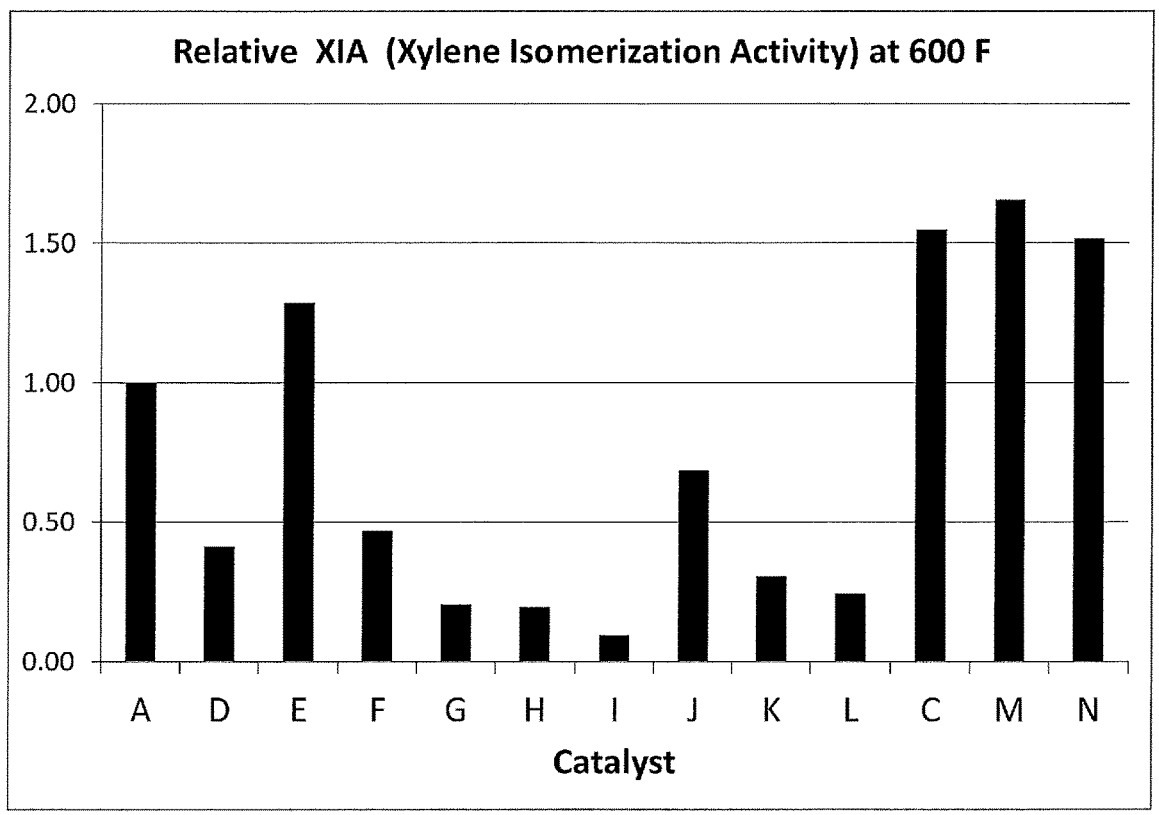
FIG. 3 shows the relative xylene isomerization activities.
Figure 4:
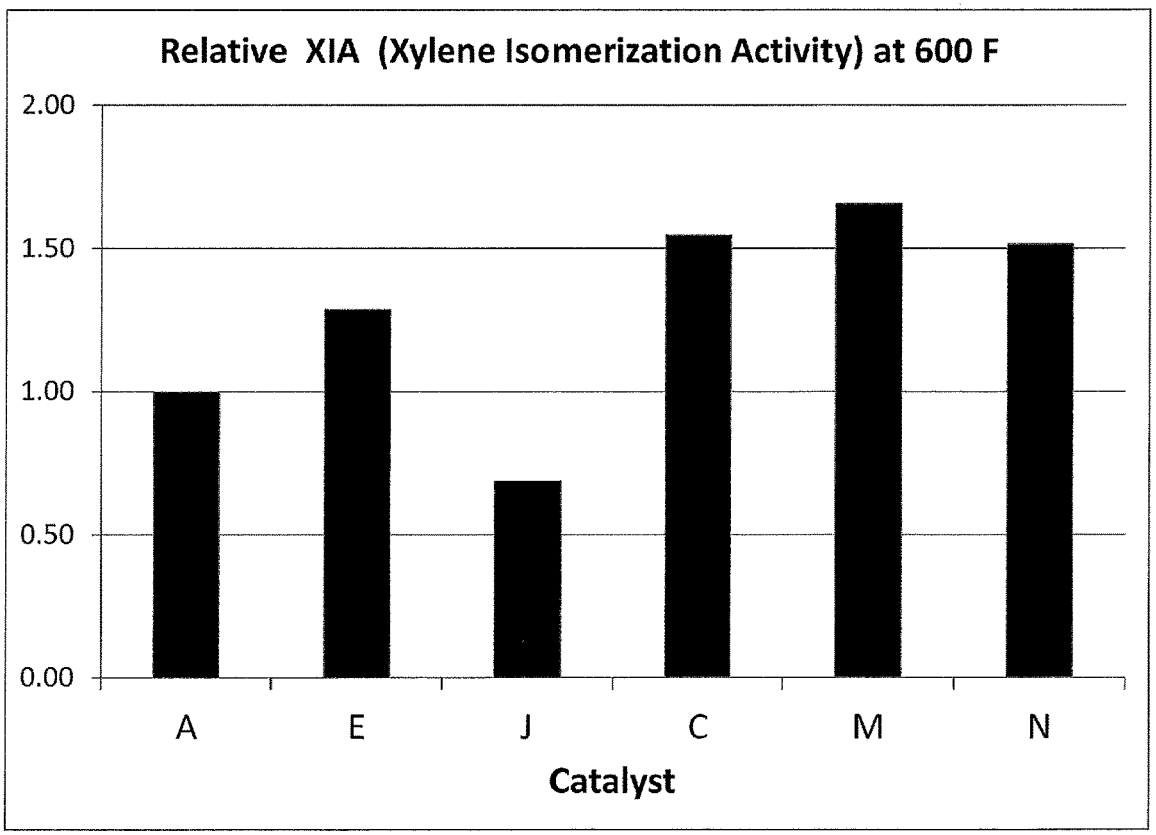
FIG. 4 shows the relative xylene isomerization activities for the six most active isomerization catalysts are shown.

In FIG. 3, the data from FIG. 2 were first converted into xylene isomerization activities (XIA) using the formula $XIA=-\ln(1-\text{fractional approach to pX equilibrium})$, then converted to relative values by dividing each by the XIA of Catalyst A (1.88). These results show that the initial isomerization activities of the Catalyst C and its two desilicated derivatives were 1.5-1.6 times greater than Catalyst A at these conditions. FIG. 4 is the same except that the multi fixed bed reactor catalyst testing instrument results for only the six most active isomerization catalysts are shown.

Figure 5:
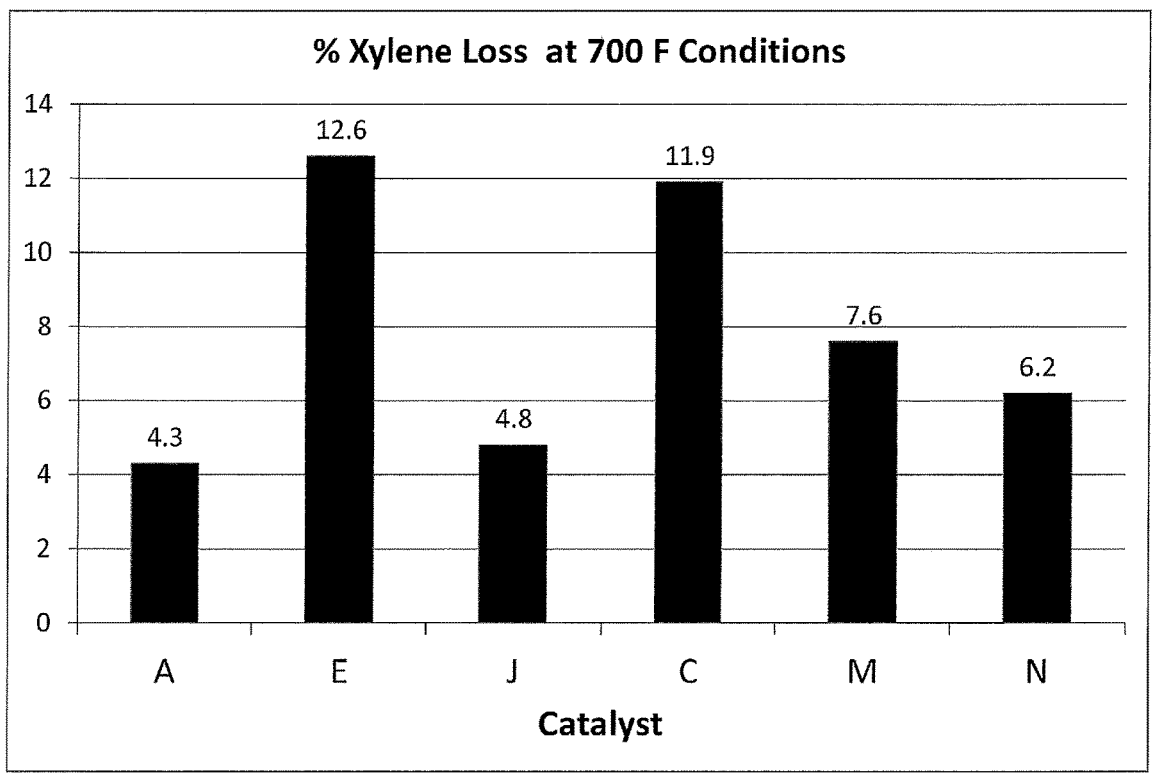
FIG. 5 shows the xylene losses observed for the six most active isomerization catalysts.
Figure 8:
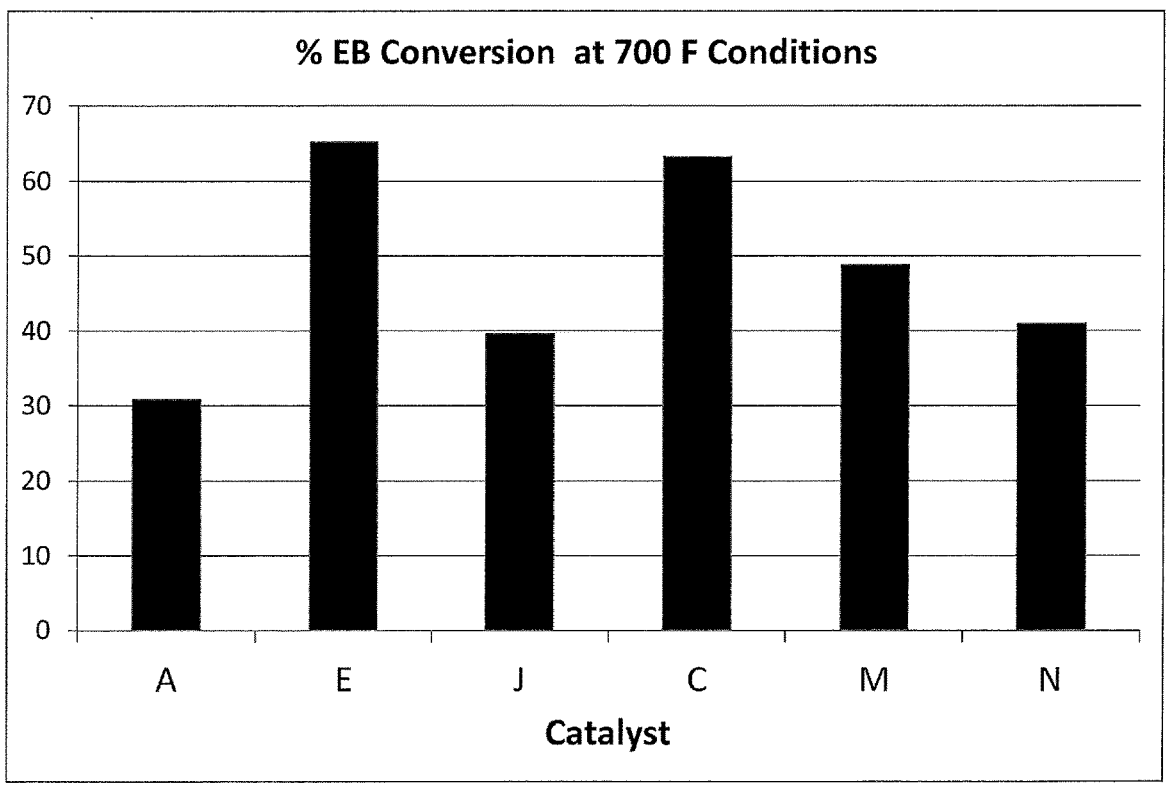
FIG. 8 shows the ethylbenzene conversions observed for Catalysts A, E, J, C, M and N.

When the multi fixed bed reactor catalyst testing instrument was switched EBC conditions (700° F., etc.), data were collected from 37-44 hours on stream in the first run and 41-48 hours on stream for the second run during which each reactor was sampled once. Results for duplicate pairs of catalysts were averaged but were in close agreement with each other. The results graphed in FIG. 5 are the xylene losses observed for the six most active isomerization catalysts. Xylene losses were calculated by the "xylenes in-xylenes out" method, meaning by comparison of xylene content in the reactor feed (blank reactor effluent) and the catalyst reactor effluent. Catalyst A and Catalyst E data shown are from the first multi fixed bed reactor catalyst testing instrument run and the other four catalysts are from the second run. Catalyst A xylene loss in the first run (4.3%) was slightly higher than in the second run (4.0%, not shown in FIG. 5). FIG. 8 is a chart of the ethylbenzene conversions observed for these catalysts. Catalyst A EB conversion in the first run (30.8%) was slightly higher than in the second run (29.0%, not shown in FIG. 8).

Figure 6:
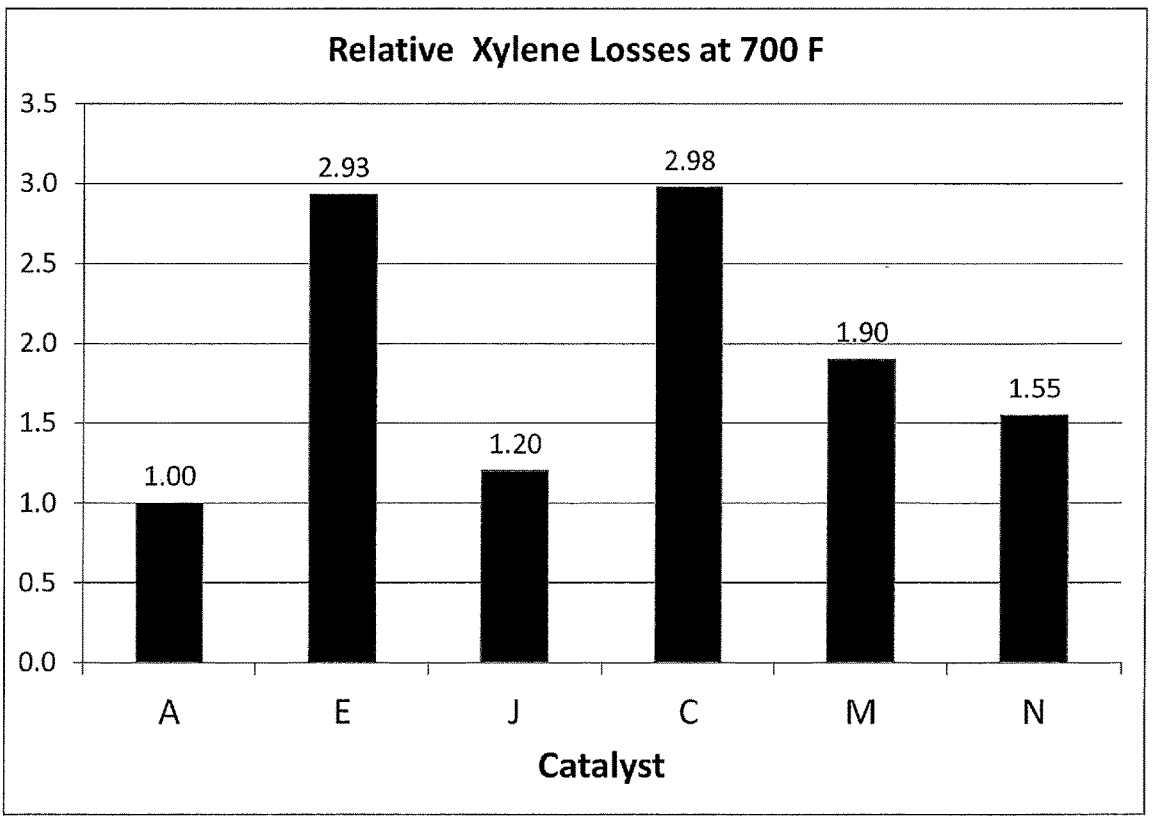
FIG. 6 shows the xylene losses relative to Catalyst A.
Figure 7:
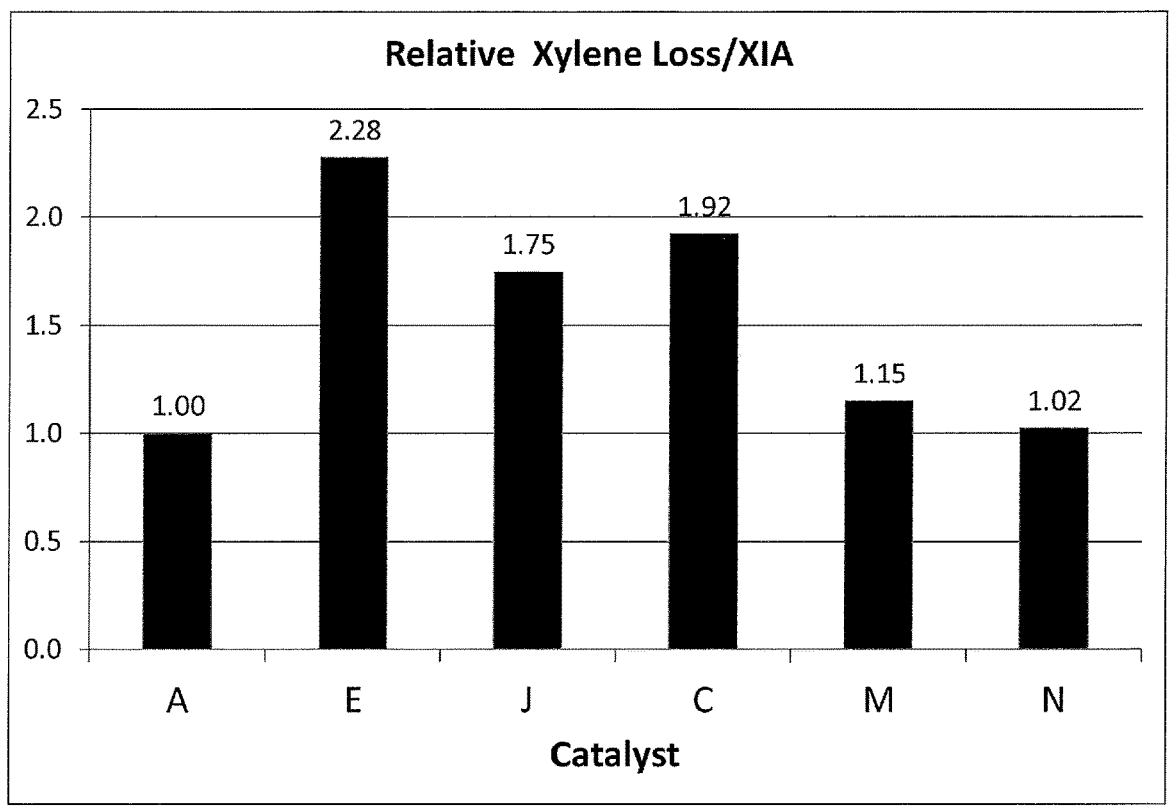
FIG. 7 shows the xylene loss/xylene isomerization activity ratio for Catalysts E, J, C, M and N relative to Catalyst A.

FIG. 6 is a graph of the xylene losses relative to Catalyst A, meaning that the xylene loss for each catalyst was divided by the Catalyst A xylene loss observed in the respective multi fixed bed reactor catalyst testing instrument run (4.3% Catalyst A xylene loss in the first run; 4.0% in the second run). The results show that all three ZSM-5's and the two desilicated derivatives displayed higher xylene losses than the Catalyst A. However, four of them also had higher xylene isomerization activity (XIA) than Catalyst A, as measured at the 600° F. conditions. Therefore, a more appropriate measure of performance is to compare xylene losses at equivalent isomerization activity. FIG. 7 is thus a chart of the Xylene Loss/XIA ratio for each catalyst relative to Catalyst A, meaning that the XL/XIA ratio for each catalyst was divided by the Catalyst A XL/XIA ratio observed in the respective multi fixed bed reactor catalyst testing instrument run (2.3 for Catalyst A in the first run; 2.1 in the second run). Xylene losses were measured at the 700° F. conditions and XIA at 600° F.

Figure 9:
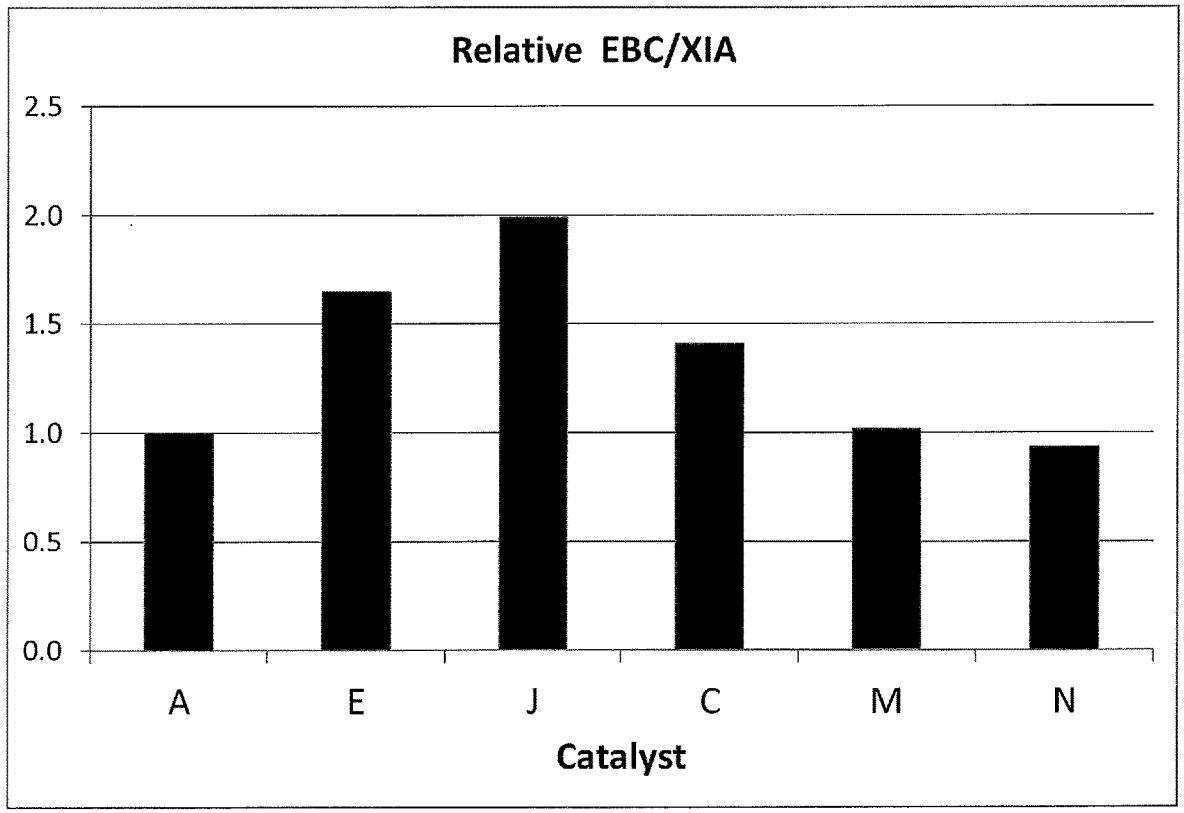
FIG. 9 shows the ethylbenzene conversion/xylene isomerization activity ratios relative to Catalyst A.

The results in FIG. 7 indicated that performance of the two desilicated ZSM-5's Catalyst M and Catalyst N were very near to that of Catalyst A with respect to xylene loss relative to isomerization activity, with the second desilicated ZSM-5 Catalyst N essentially the same as Catalyst A. A very similar trend is seen in the relative EBC/XIA ratios shown in FIG. 9.

Figure 10:
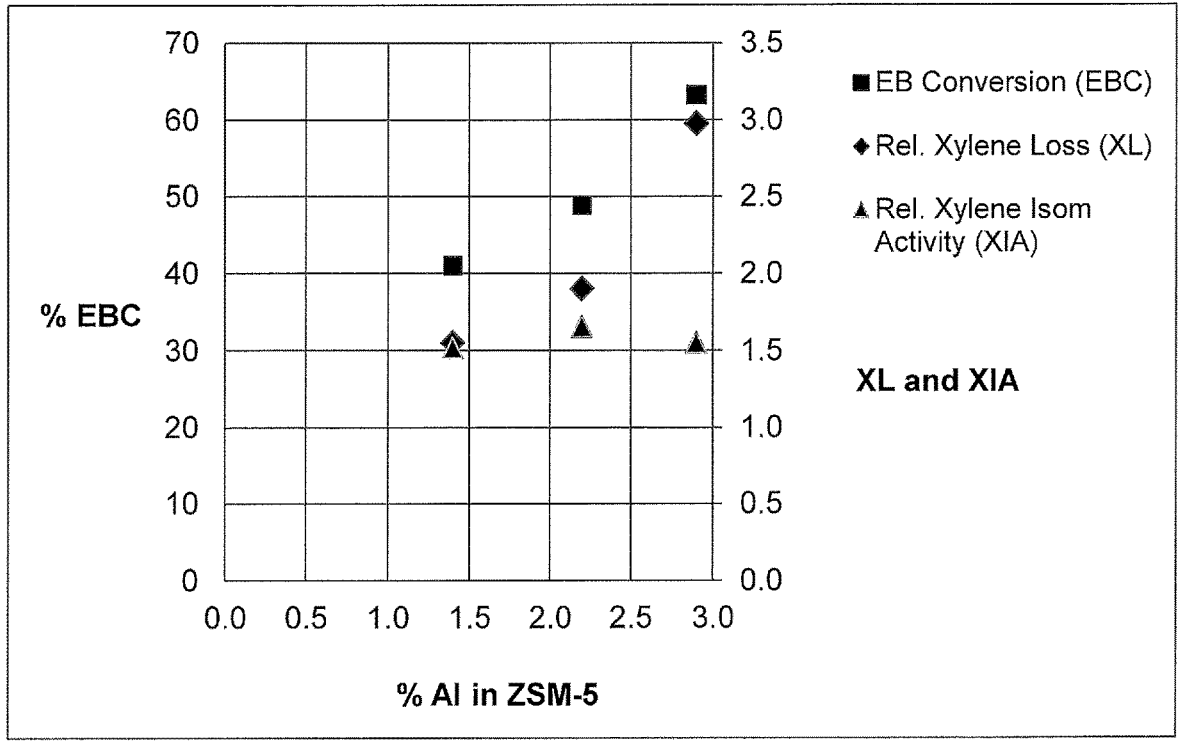
FIG. 10 shows the ethylbenzene conversions and xylene losses of parent Catalyst C and desilicated catalysts Catalyst M and Catalyst N.

The desilication procedure employed also caused partial dealumination of the parent ZSM-5 Catalyst C, as seen in the ICP data in Table I. The EB conversions and xylene losses of the parent Catalyst C and desilicated catalysts Catalyst M and Catalyst N were roughly proportional to zeolite aluminum content (and Bronsted acidity) as shown in FIG. 10.

Desilications of two other ZSM-5's were performed: Catalyst E and Catalyst J. Catalyst E was the other zeolite that showed higher isomerization activity than Catalyst A in the initial screening discussed above, while the Catalyst J was moderately less active than Catalyst A. The synthetic procedures employed were similar to those described above and some of the details of the caustic treatment are given in Table II. The NaOH desilication employed a 3% solids (zeolite powder) concentration in the caustic solution. Following the NaOH desilication treatment, the solid product was collected by filtration, washed with water, dried, treated with a 10 wt % aqueous oxalic acid solution at room temperature for 4 hours, washed, dried, and calcined at 510° C. Analytical data for the calcined products are given in Table II. Catalytic tests were performed of the powder products using the multi fixed bed reactor catalyst testing instrument instrument as described previously. The multi fixed bed reactor catalyst testing instrument runs began at Isom conditions for a day, switched to EBC conditions for 1-2 days, then back to Isom conditions. Xylene loss (XL) and ethylbenzene conversion results were taken from the last several hours at EBC conditions, while isomerization results (XIA, pX/X) were taken from the initial several hours upon return to Isom conditions after EBC. Table II also has a summary of the multi fixed bed reactor catalyst testing instrument catalytic results. Selectivity (xylene loss) was measured as the XL/XIA ratio relative to that of the Catalyst A reference in the multi fixed bed reactor catalyst testing instrument run.

TABLE II

Desilications of J and E

| ZSM-5 and Desilication Conditions | Yield % | XRD Cryst % | ICP Al wt % | SAR | Na ppm | N$_2$ Ads Mesopore S.A. m$^2$/g | N$_2$ Ads Micropore vol. cc/g | Catalytic Rel. Rel. XIA[a] | Catalytic Rel. XL/XIA[b] |
|---|---|---|---|---|---|---|---|---|---|
| J | | 95 | 1.44 | 56 | | 148 | 0.143 | 0.79 | 1.67 |
| J1 45 C., 0.5M NaOH, 30 min | 38 | 80 | 1.25 | 62 | 471 | 174 | 0.135 | 1.05 | 1.25 |
| J2 65 C., 0.5M NaOH, 30 min | 20 | 47 | 0.89 | 88 | 292 | 312 | 0.133 | 0.78 | 1.24 |
| J3 85 C., 0.5M NaOH, 30 min | 12 | 30 | 0.65 | 122 | 370 | 252 | 0.120 | | |
| E | | 85 | 2.16 | 37 | 67 | 164 | 0.121 | 1.39 | 2.33 |
| E1 45 C., 0.5M NaOH, 30 min | 58 | 83 | 1.97 | 38 | 336 | 185 | 0.125 | 1.78 | 1.85 |
| E2 55 C., 0.5M NaOH, 30 min | 48 | 79 | 1.94 | 38 | 389 | 198 | 0.134 | 1.65 | 1.61 |
| E3 65 C., 0.5M NaOH, 30 min | 35 | 61 | 1.52 | 51 | 290 | 266 | 0.127 | 1.54 | 1.16 |
| E4 75 C., 0.5M NaOH, 30 min | 23 | 35 | 0.89 | 86 | 333 | 329 | 0.119 | 0.87 | 0.83 |
| E5 85 C., 0.5M NaOH, 30 min | 18 | 21 | 0.56 | 142 | 249 | 285 | 0.115 | 0.23 | 1.44 |

[a]Xylene Isomerization Activity (XIA) relative to that of A as measured at "Isom" conditions (600° F., 225 psig, 1.5/1 H$_2$/HC mole ratio)
[b]Ratio of Xylene Loss (XL) to XIA relative to that of A, with XL measured at "EBC" conditions (700° F., 200 psig, 2/1 H$_2$/HC mole ratio) and XIA measured at "Isom" conditions.

Catalyst J: Results showed that desilication could improve its isomerization activity (XIA) modestly to that of Catalyst A, but not higher and not to the activity levels of the two other zeolites (Catalyst C and Catalyst E). The lowest XL/XIA ratio we observed was about 25% higher than the Catalyst A reference.

Catalyst E: As seen in Table II, it was possible to achieve xylene losses lower than Catalyst A (relative XL/XIA=0.83) by a relatively severe desilication in which the synthetic yield was only 23%. Desilications at lower temperatures gave higher yields but less selective catalysts. However, the isomerization activity of the 23%-yield desilicated zeolite was about 13% lower than the Catalyst A.

More desilications of the Catalyst C zeolite were performed with varying desilication procedures with 3 wt % initial solids. The new desilications are those identified as Catalysts R, S & T in Tables III and IV and those in Table V (Catalysts U, V, W, X, and Y). Procedures employed were similar to those described previously but with different caustic treatment conditions and some variation of the oxalic acid treatment conditions as well. Catalytic tests were performed of the pure zeolite powder products using the multi fixed bed reactor catalyst testing instrument.

TABLE III

Desilications of C

| Desilicated ZSM-5 from C | NaOH conc. (M) | Solids Conc. in NaOH Mixture | NaOH Treatment Time, Temp | Solids Conc. in Oxalic Acid Mixture[1,2] | Oxalic Acid Treatment Time, Temp | Final Yield after calcination |
|---|---|---|---|---|---|---|
| M | 0.5 | 6 wt % | 1.5 h, 85° C. | 8 wt % | 2 h, 70° C. | 48% |
| N | 0.5 | 3 wt % | 1.5 h, 85° C. | 8 wt % | 2 h, 70° C. | 22% |
| R | 0.5 | 3 wt % | 0.5 h, 85° C. | 8 wt % | 4 h, r.t. | 39% |
| S | 0.5 | 3 wt % | 0.5 h, 75° C. | 8 wt % | 4 h, r.t. | 55% |
| T | 0.5 | 3 wt % | 0.5 h, 65° C. | 8 wt % | 4 h, r.t. | 65% |

[1]Nominal solids concentration calculated based on amount of ZSM-5 prior to caustic treatment. Actual solids concentration was lower due to ZSM-5 mass loss from caustic treatment.
[2]Oxalic acid solution concentration was 9 wt % based on oxalic acid dihydrate in water.

TABLE IV

Desilications of C

| ZSM-5 Sample[a] | ICP | | | | | XRD | N$_2$ Physisorption | | | | |
| --- | --- | --- | --- | --- | --- | --- | --- | --- | --- | --- | --- |
| | Al (ppm) | Na (ppm) | Si (ppm) | SAR[b] | Al wt % calc.[c] | % Cryst.[d] | Total SA (m$^2$/g) | Meso-Pore SA (m$^2$/g) | Total Pore vol (cc/g) | Micropore vol (cc/g) | Meso-Pore vol (cc/g) |
| C | 24883 | 117 | 385300 | 30 | 2.9 | 94 | 457 | 103 | 0.440 | 0.144 | 0.296 |
| M | 20617 | 80 | 416600 | 39 | 2.2 | 71 | 544 | 209 | n.d. | 0.137 | n.d. |
| N | 12560 | 155 | 417700 | 64 | 1.4 | 58 | 604 | 263 | 1.103 | 0.148 | 0.955 |
| R | 20900 | 83 | 403900 | 37 | 2.3 | 39 | 564 | 251 | 0.816 | 0.130 | 0.686 |
| S | 23540 | 47 | 401100 | 33 | 2.6 | 55 | 515 | 199 | 0.558 | 0.130 | 0.428 |
| T | 23790 | 61 | 405100 | 33 | 2.6 | 65 | 494 | 161 | 0.544 | 0.137 | 0.407 |

[a]analyzed after calcination at 510° C.
[b]SiO$_2$/Al$_2$O$_3$ mole ratio calculated from ICP data
[c]calculated from Al and Si oxides from ICP data
[d]relative to a reference ZSM-5

TABLE V

Desilications of U at 3 wt % Solids

| ZSM-5 and Desilication Conditions[d] | Yield % | XRD Cryst % | ICP | | | | N$_2$ Ads | | Catalytic | |
| --- | --- | --- | --- | --- | --- | --- | --- | --- | --- | --- |
| | | | Al wt % | SAR[a] | Na ppm | | Mesopore S.A. m$^2$/g | Micropore vol. cc/g | Rel. XIA[b] | Rel. XL/XIA[c] |
| U | | 92 | 2.88 | 26 | 251 | | 100 | 0.149 | | |
| V 85 C., 0.5M NaOH, 30 min | 43 | 78 | 2.16 | 34 | 80 | | 233 | 0.131 | 1.89 | 1.46 |
| W 85 C., 0.5M NaOH, 30 min | 43 | 78 | 2.21 | 34 | 74 | | 235 | 0.129 | 1.94 | 1.50 |
| X 85 C., 0.25M NaOH, 30 min | 61 | 89 | 2.51 | 29 | 48 | | 162 | 0.142 | 1.69 | 1.78 |
| Y 85 C., 0.1M NaOH, 30 min | 76 | 93 | 2.56 | 30 | 30 | | 150 | 0.137 | 1.54 | 1.94 |

[a]SiO$_2$/Al$_2$O$_3$ mole ratio
[b]Xylene Isomerization Activity (XIA) relative to that of A as measured at "Isom" conditions (600° F., 225 psig, 1.5/1 H$_2$/HC mole ratio)
[c]Ratio of Xylene Loss (XL) to XIA relative to that of A, with XL measured at "EBC" conditions (700° F., 200 psig, 2/1 H$_2$/HC mole ratio) and XIA measured at "Isom" conditions.
[d]After desilication, the oxalic acid solution treatment was performed for 4 hours at room temperature.

Figure 11:
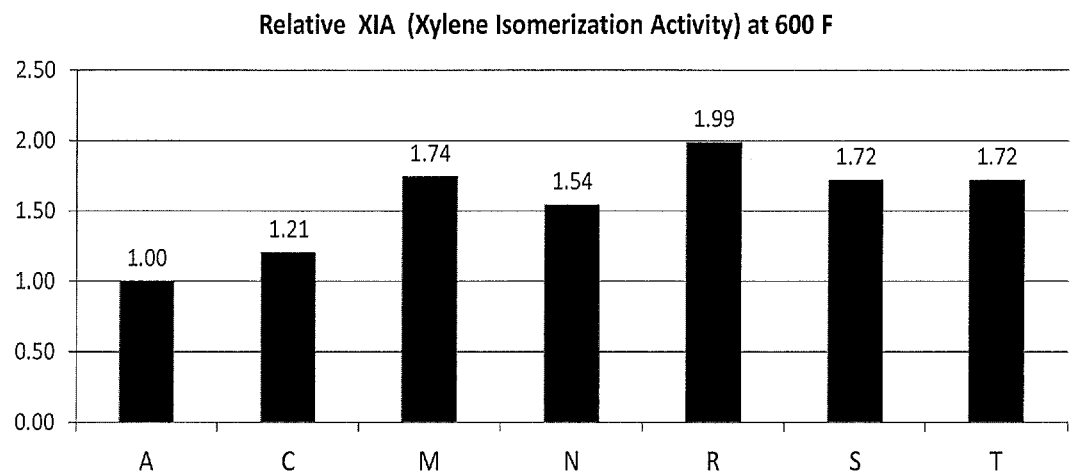
FIG. 11 shows isomerization activities of Catalysts A, C, and Desilicated Variants of Catalyst C.
Figure 12:
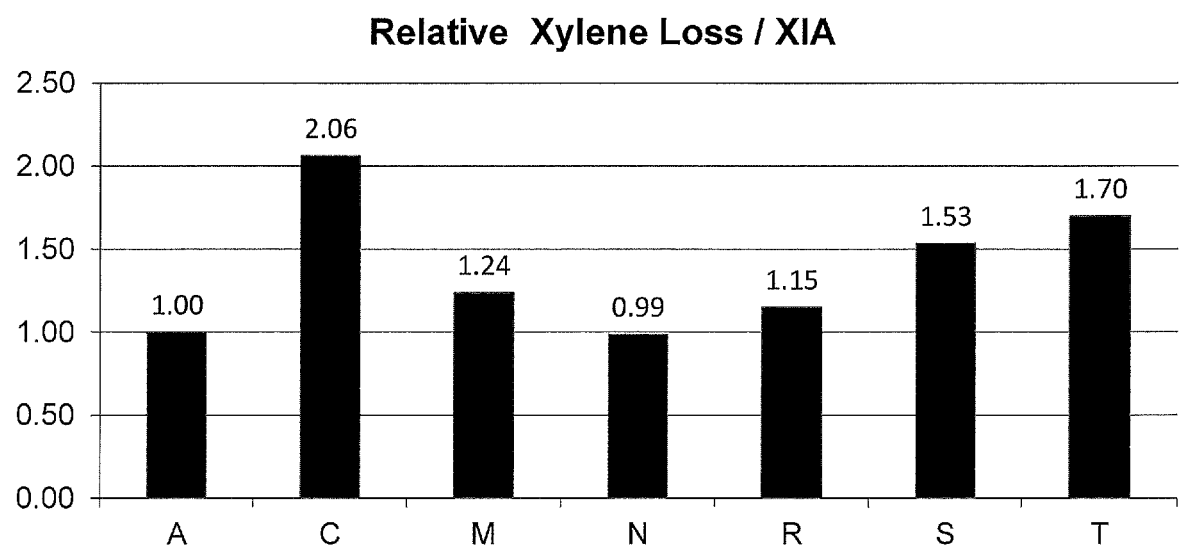
FIG. 12 shows xylene losses expressed as the ratio of xylene loss to xylene isomerization activity relative to Catalyst A performance.

Desilications leading to Catalysts R, S & T were performed with varying reaction temperature (65-85° C.), similar in procedure to Catalyst N but with only 0.5-hour NaOH exposure times at temperatures and using room temperature oxalic acid treatments. Yields ranged from about 40% to 65%, inversely proportional to the caustic acid treatment temperature. Catalytic results are shown in FIGS. 11 and 12. All three of these new desilicated catalysts exhibited higher xylene isomerization activity than the Catalyst A, with Catalyst R about twice as active as Catalyst A. Xylene losses are expressed as the ratio of xylene loss to XIA (xylene isomerization activity) relative to Catalyst A performance (FIG. 12). Catalysts with the highest mesoporosities displayed the lowest xylene losses relative to their isomerization activity. The desilication of Catalyst N showed essentially the same xylene loss/XIA ratio as Catalyst A, while the desilication Catalyst M and Catalyst R were higher. The effect of NaOH concentration (0.1-0.5 M) was explored in Table V.

Figure 13A:
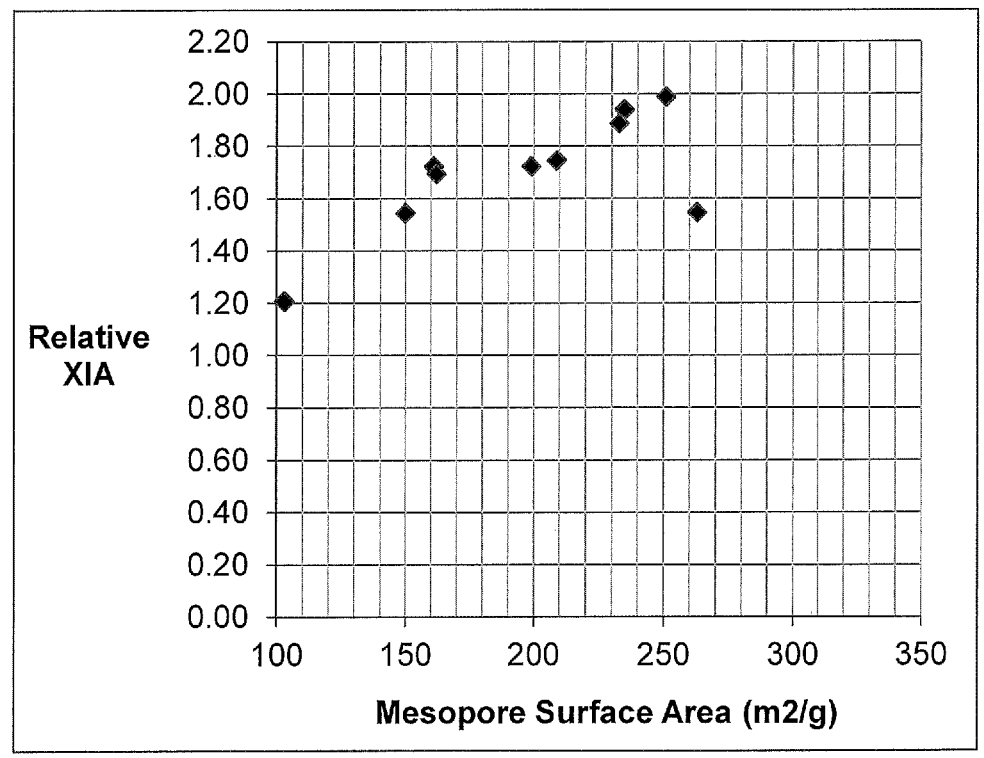
FIG. 13a shows relative xylene isomerization activity versus mesopore surface area of a desilicated ZSM-5 catalyst.
Figure 13B:
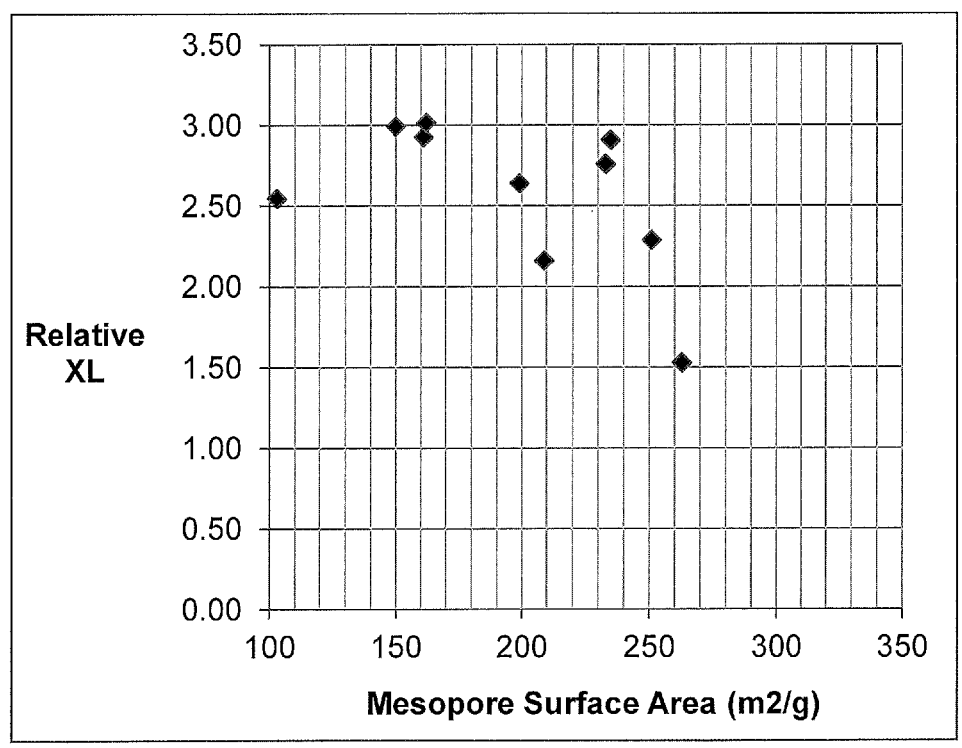
FIG. 13b shows relative xylene loss versus mesopore surface area of a desilicated ZSM-5 catalyst.
Figure 13C:
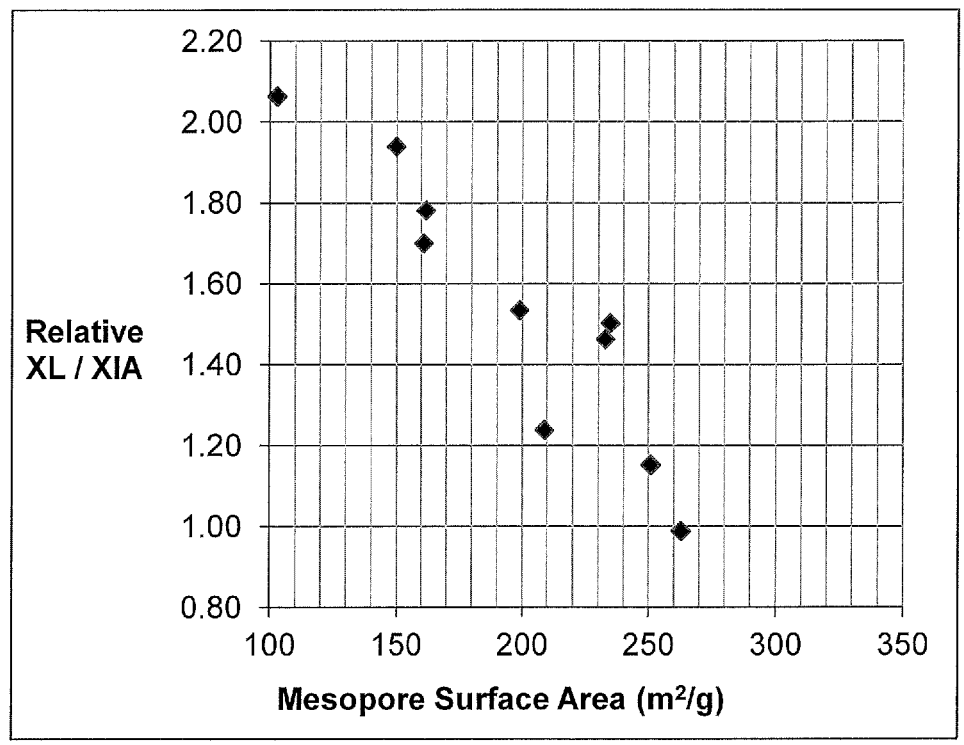
FIG. 13c shows relative xylene loss/xylene isomerization activity versus mesopore surface area of a desilicated ZSM-5 catalyst.

FIGS. 13a, 13b, 13c, 13d, 13e and 13f shows six plots of the results of these various desilicated Catalyst C experiments. The XIA, XL, and XL/XIA values were calculated relative to Catalyst A with Catalyst A=1.0 on the scale. The parent Catalyst C is represented by the points with the lowest mesopore surface area (100 m$^2$/g) or 100% yield (no desilication). FIG. 13a shows a general trend of increasing xylene isomerization activity with higher mesopore (external) surface area. The drop in activity of the catalyst with the highest surface area (desilication Catalyst N of Tables III and IV) is likely due to its relatively low Al content compared to the others. FIG. 13b shows no real trend of xylene loss with mesopore surface area, excluding the rightmost point which again is the catalyst with relatively low Al (desilication Catalyst N). However, FIG. 13c shows a clear decrease in xylene loss relative to isomerization activity as mesopore surface area increases.

Figure 13D:
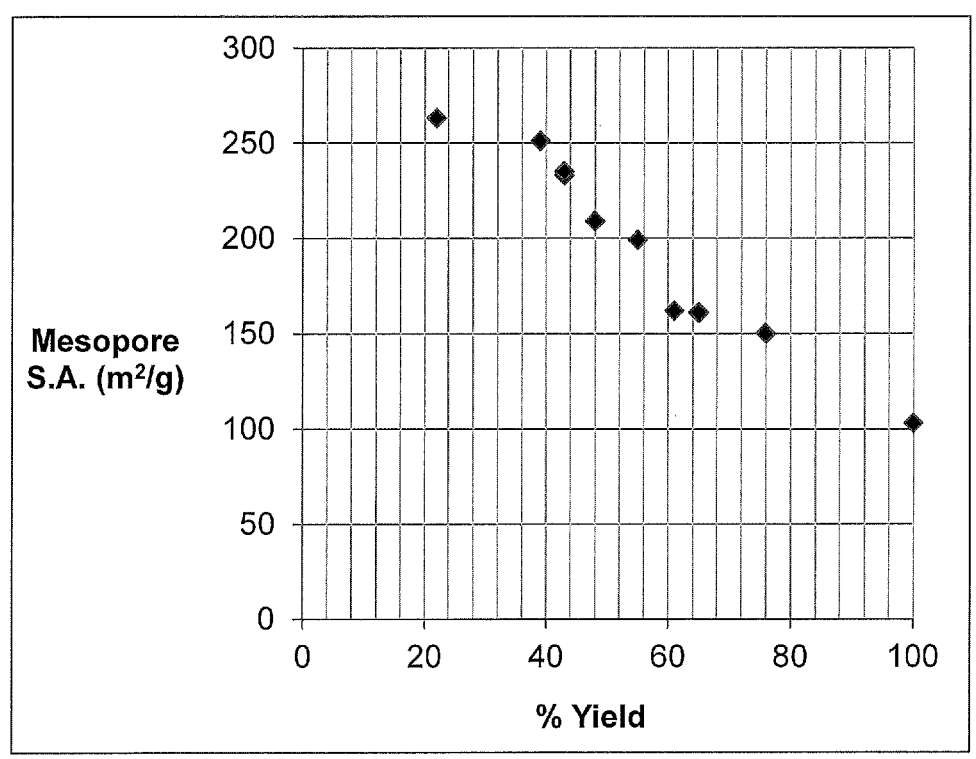
FIG. 13d shows mesopore surface area versus % yield of a desilicated ZSM-5 catalyst.
Figure 13E:
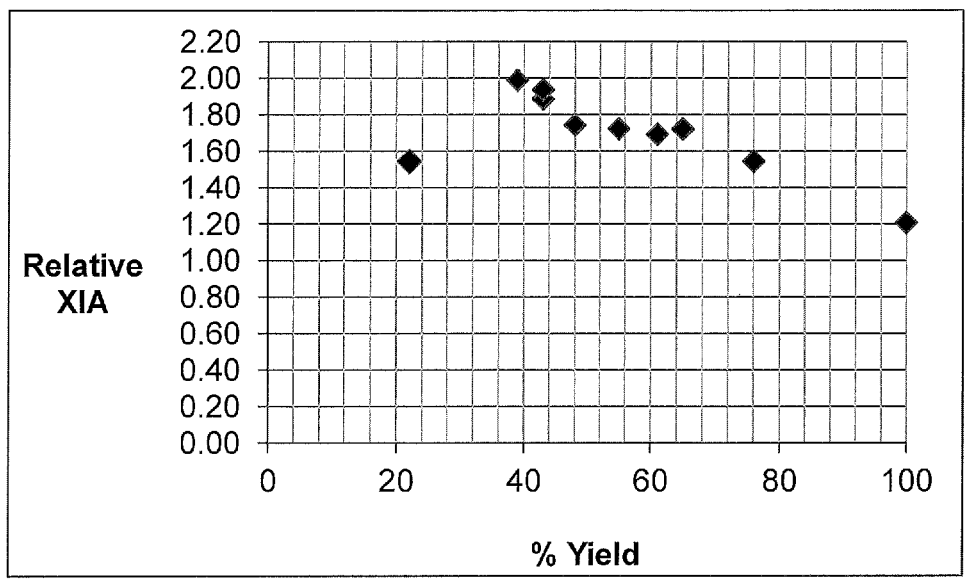
FIG. 13e shows relative xylene isomerization activity versus % yield of a desilicated ZSM-5 catalyst.
Figure 13F:
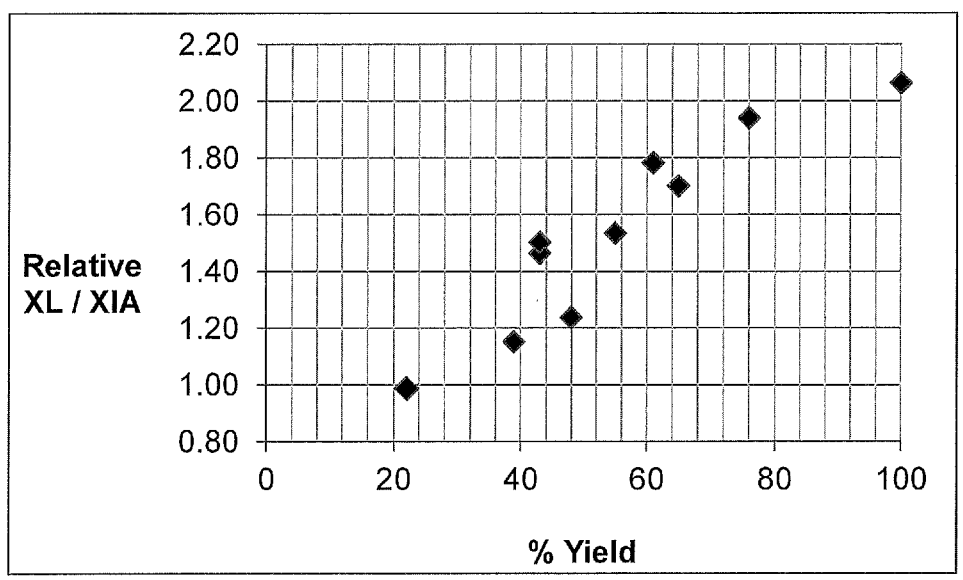
FIG. 13f shows relative xylene loss/xylene isomerization activity versus % yield of a desilicated ZSM-5 catalyst.

FIGS. 13d, 13e and 13f show various trends with desilication yield. Lower yield (more zeolite dissolution) due to increasing severity of the desilication conditions (higher temperature, higher NaOH concentration, longer time) resulted in higher mesoporosity. FIGS. 13e and 13f show XL and XL/XIA as a function of yield instead of mesoporosity.

Synthetic yields of the most selective (lowest XL/XIA) desilicated catalysts (Catalysts M, N and R) were around 22-48%.

Scale Up: The basic procedure was similar to that of desilicating Catalyst N but employed a jacketed 3-liter round-bottom glass vessel for the desilication and the reaction was initiated by adding a small amount of 50 wt % NaOH solution to a preheated zeolite/water mixture. Using an addition funnel, 77.6 g of 50 wt % NaOH solution was added to a mechanically stirred mixture of Catalyst U powder (60 g) in water (1900 g) that had been preheated to 85° C. in the jacketed 3-liter vessel. The mixture was stirred for 2 hours at 85° C., then drained into a separate vessel and cooled to 40° C. over ~25 minutes using chilled water glass heat exchanger, filtered, washed with DI water (4×180 mL), and dried. The dried material was then stirred in a solution of 60 g of oxalic acid dihydrate in 600 g DI water at room temperature for 4 hours or at 70° C. for 2 hours, followed by filtering, washing (4×180 mL DI water), drying, and calcination at 510° C.

Four desilicated ZSM-5's catalysts Catalysts AA, BB, CC, and DD were prepared identically in reproducible yields of 26-27% (Table VI). Analyses and multi fixed bed reactor catalyst testing instrument catalytic results of these were very similar, indicating good synthetic reproducibility. These four were prepared using 70° C. oxalic acid treatment after desilication. They showed lower Al content and slightly lower xylene losses (XL/XIA) than Catalyst Z which had been prepared using room temperature oxalic acid treatment. The higher temperature acid treatment was more effective at removal of aluminum from the desilicated zeolites.

Multi fixed bed reactor catalyst testing instrument catalytic tests of the powder products were performed similarly to before except that the runs began at EBC conditions (instead of at Isom conditions) for 2 days and then switched to Isom conditions for 1 day.

Initial experiments followed the same desilication procedure as employed previously for 3% solids desilications: heat an aqueous mixture of Catalyst U ZSM-5 powder to 85° C., add an aliquot of 50% NaOH solution, mix at 85° C. for 2 hours, cool, filter, and wash with water. This was followed by treatment with 10% oxalic solution at 70° C. for 2 hours, filtering, washing, drying, and calcination. The principal difference was that a more concentrated mixture was used in which the ZSM-5 powder constituted 15 wt % of the initial mixture after addition of NaOH. Because the desilication reaction is stoichiometric in NaOH, however, approximately the same relative amount of NaOH and ZSM-5 was employed as the earlier 3% solids experiments. This resulted in a much higher initial NaOH concentration in the reaction mixture (~2 M) than in the 3% solids experiments (0.5 M).

Table VII summarizes details of how these experiments were conducted along with characterization data and multi fixed bed reactor catalyst testing instrument test results of the desilicated products obtained. The first data row is that of untreated Catalyst U and the two rows below in gray shading are two previous experiments with 3% solids. The next four rows down (experiments 1-4) are 15% solids experiments with varying amounts of NaOH, all of which was added at the start of the desilication reaction. The product yields were inversely correlated with the amount of NaOH employed. Three of the four products were much

TABLE VI

Scaled-up Desilications of U at 3 wt % Solids

| Desilication Conditions | ID | Yield % | XRD Cryst % | ICP Al wt % | SAR$^a$ | Na ppm | N$_2$ Ads Mesopore S.A. m$^2$/g | Micropore vol. cc/g | Catalytic Rel. XIA$^b$ | Rel. XL/XIA$^c$ |
|---|---|---|---|---|---|---|---|---|---|---|
| U | U | | 92 | 2.81 | 28 | 242 | 137 | 0.120 | 1.2 | 2.1 |
| 85 C., 0.5M NaOH, 2 hrs, 60 g ZSM-5; then oxalic acid treatment 4 h at r.t. | Z | 26 | 54 | 1.69 | 48 | 185 | 328 | 0.098 | 1.8 | 1.1 |
| 85 C., 0.5M NaOH, 2 hrs, 60 g ZSM-5; oxalic acid treatment 2 h at 70 C. | AA | 26 | 54 | 1.64 | 52 | 155 | 278 | 0.121 | 1.4 | 1.0 |
| 85 C., 0.5M NaOH, 2 hrs, 60 g ZSM-5; oxalic acid treatment 2 h at 70 C. | BB | 26 | 52 | 1.50 | 54 | 191 | 317 | 0.106 | not done | not done |
| 85 C., 0.5M NaOH, 2 hrs, 60 g ZSM-5; oxalic acid treatment 2 h at 70 C. | CC | 27 | 53 | 1.52 | 51 | 176 | 337 | 0.090 | 1.5 | 1.0 |
| 85 C., 0.5M NaOH, 2 hrs, 60 g ZSM-5; oxalic acid treatment 2 h at 70 C. | DD | 26 | 51 | 1.56 | 54 | 165 | 280 | 0.121 | 1.4 | 1.1 |

$^a$SiO$_2$/Al$_2$O$_3$ mole ratio
$^b$Xylene Isomerization Activity (XIA) relative to that of A as measured at "Isom" conditions (600° F., 225 psig, 1.5/1 H$_2$/HC mole ratio)
$^c$Ratio of Xylene Loss (XL) to XIA relative to that of A, with XL measured at "EBC" conditions (700° F., 200 psig, 2/1 H$_2$/HC mole ratio) and XIA measured at "Isom" conditions.

Most previous desilications employed 3 wt % zeolite solids in the zeolite/NaOH solution reaction mixture. Raising this to 15% initial solids would produce 5-fold higher yields for the same scale reaction.

lower in crystallinity and Al content than the 3% solids products. All four were significantly lower in xylene isomerization activity (XIA) and worse in xylene loss selectivity (XL/XIA) than the 3% solids products.

TABLE VII

Desilications of U at 15 wt % Solids

| Exp # | ZSM-5 amount | Amount of 50% NaOH Added and Method of Addition | ID | XRD Yield % | Cryst % | ICP Al wt % | Na ppm | N₂ Ads Meso-pore S.A. m²/g | Micro-pore vol. cc/g | Catalytic Rel. XIA[a] | Rel. XL/XIA[b] |
|---|---|---|---|---|---|---|---|---|---|---|---|
| | parent | None | U | | 92 | 2.81 | 242 | 137 | 0.120 | 1.2 | 2.1 |
| | 3% solids | full initial addition, 0.5M | CC | 27 | 53 | 1.7 | 176 | 337 | 0.090 | 1.53 | 1.02 |
| | 3% solids | full initial addition, 0.5M | DD | 26 | 51 | 1.6 | 165 | 280 | 0.121 | 1.40 | 1.07 |
| 1 | 20 g (15 wt %) | 20 g, full initial addition | FF | 16.6 | 25 | 0.87 | 157 | 258 | 0.137 | 0.56 | 1.23 |
| 2 | 20 g (15 wt %) | 18 g, full initial addition | GG | 22.1 | 35 | 1.22 | 124 | 233 | 0.133 | 0.89 | 1.16 |
| 3 | 20 g (15 wt %) | 16 g, full initial addition | HH | 30.7 | 48 | 1.61 | 102 | 221 | 0.128 | 1.11 | 1.25 |
| 4 | 20 g (15 wt %) | 17 g, full initial addition | II | 25.5 | 41 | 1.41 | 121 | 248 | 0.125 | 1.02 | 1.21 |
| 5 | 50 g (15 wt %) | 42.5 g, four 10.6-g doses added every 30 min | JJ | 30.5 | 55 | 1.72 | 148 | 251 | 0.127 | 1.41 | 1.12 |
| 6 | 50 g (15 wt %) | 42.5 g, seven 6.1-g doses added every 15 min | KK | 31.0 | 53 | 1.72 | 151 | 259 | 0.123 | 1.42 | 1.10 |
| 7 | 50 g (15 wt %) | 48.6 g, four 12.2-g doses added every 30 min | LL | 24.2 | 46 | 1.54 | 201 | 301 | 0.120 | 1.26 | 1.10 |

[a]Xylene Isomerization Activity (XIA) relative to that of A as measured at "Isom" conditions (600° F., 225 psig, 1.5/1 H₂/HC mole ratio)
[b]Ratio of Xylene Loss (XL) to XIA relative to that of A, with XL measured at "EBC" conditions (700° F., 200 psig, 2/1 H₂/HC mole ratio) and XIA measured at "Isom" conditions.

The relatively low crystallinities, Al content, and catalytic performance may be due to the very high initial NaOH concentrations employed in these four experiments compared to the earlier 3% solids desilications. The mesopore (or external) surface areas measured for these products were in fact less than those of the 3% solids products. Surprisingly it has been found that adding NaOH gradually or in small doses over time rather than all at once in order to keep the solution NaOH concentration relatively low at all times provides increased mesopore formation.

Shown in the lowest three rows of Table VII (experiments 5-7) are data for 15% solids experiments that were performed similarly to those above except that small doses of 50% NaOH were added to the reaction mixture at intervals of 15 or 30 minutes. Total reaction time at 85° C. was still 2 hours. Experiments 5 and 6 employed the same total amount of NaOH relative to ZSM-5 as experiment 4. The results show that the staged-addition experiments 5 and 6 gave higher yields than experiment 4 and also generated desilicated products that were more crystalline and higher in Al content than experiment 4. Importantly, the catalytic performance of the products of experiments 5 and 6 were significantly improved over those of all the "full initial addition" 15% solids experiments (1-4). In fact, the isomerization activities (XIA) and xylene loss selectivities (XL/XIA) of experiments 5 and 6 were close to those obtained in the earlier 3% solids experiments.

The only difference between experiments 5 and 6 was the NaOH dose frequency and amount. The use of smaller, more frequent doses in experiment 6 yielded virtually the same results in all respects as experiment 5 which employed only four doses spaced at 30-minute intervals.

About 15% more NaOH was employed in experiment 7 to obtain a lower yield (24%) than experiments 5 and 6 (31%). A multi fixed bed reactor catalyst testing instrument test of this catalyst showed it to have ~10% lower activity than those of experiment 5 and 6, likely due to its Al content being ~10% lower, but very similar xylene loss selectivity (1.1 XL/XIA).

Cabosil silica-supported, Mo-containing catalysts were prepared for pilot plant testing of performance and aging vs. Catalyst B. These catalysts consisted of a 20:80 ratio of desilicated ZSM-5/silica with 2 or 4 wt % Mo added by wet impregnation of a mixture of ZSM-5 and HS-5 cabosil powders with aqueous ammonium heptamolybdate and subsequent calcination to Mo oxide.

Table VIII has the analytical characterization data for three such catalysts that were prepared and multi fixed bed reactor catalyst testing instrument test results compared to Catalyst B reference. All three catalysts showed high isomerization activity relative to Catalyst B in the multi fixed bed reactor catalyst testing instrument.

TABLE VIII

Mo-Desilicated ZSM-5/Silica Catalysts (20:80 ZSM-5:silica)

| Desilicated ZSM-5 Starting Material | Cat. ID | Target Mo % | XRD Cryst % | ICP Al wt % | ICP Mo wt % | ICP Na ppm | N$_2$ Ads Mesopore S.A. m$^2$/g | N$_2$ Ads Micropore vol. cc/g | Catalytic Rel. XIA[a] | Catalytic Rel. XL/XIA[b] |
|---|---|---|---|---|---|---|---|---|---|---|
| AA | EE | 2 | 13 | 0.29 | 2.0 | 76 | 310 | 0.016 | 1.6 | 1.2 |
| CC | O | 2 | 13 | 0.28 | 2.4 | 94 | 259 | 0.018 | 2.0 | 1.2 |
| DD | P | 4 | 14 | .29 | 5.0[c] | 155 | 240 | 0.028 | 1.6 | 1.1 |

[a] Xylene Isomerization Activity (XIA) relative to that of B as measured at "Isom" conditions (600° F., 225 psig, 1.5/1 H$_2$/HC mole ratio)
[b] Ratio of Xylene Loss (XL) to XIA relative to that of B, with XL measured at "EBC" conditions (700° F., 200 psig, 2/1 H$_2$/HC mole ratio) and XIA measured at "Isom" conditions.
[c] 4.1 wt % Mo by XRF Two-week pilot plant tests were done of Catalyst B (4.0-gram charge) and desilicated Mo-ZSM-5/silica catalysts Catalyst EE (2% Mo, 2.3-g charge) and Catalyst P (4% Mo, 2.0-g charge). Catalyst charges were chosen based on multi fixed bed reactor catalyst testing instrument activity results. All runs were performed identically, beginning at "Isom" conditions for 2 days (600° F., 225 psig, 1.5 H$_2$/HC ratio, 152 g/h liquid feed), switching to "EBC" conditions for 5 days (700° F., 200 psig, 2.0 H$_2$/HC ratio, 40 g/h liquid feed), back to Isom conditions for 1 day, then EBC conditions again for 6 days, and finally back to Isom conditions for 2 final days. The same absolute liquid and H$_2$ rates were employed in both runs despite the different catalyst weight loadings. One sample was taken per day.

Figure 14A:
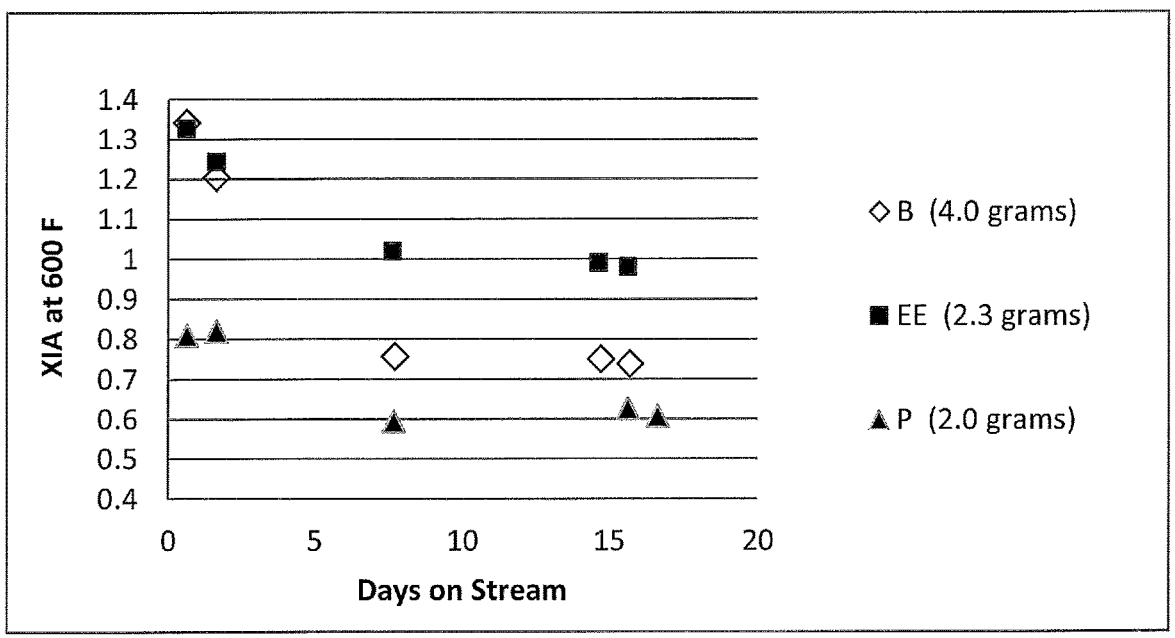
FIG. 14a shows xylene isomerization activity versus days on stream of Catalysts B, EE and P.
Figure 14B:
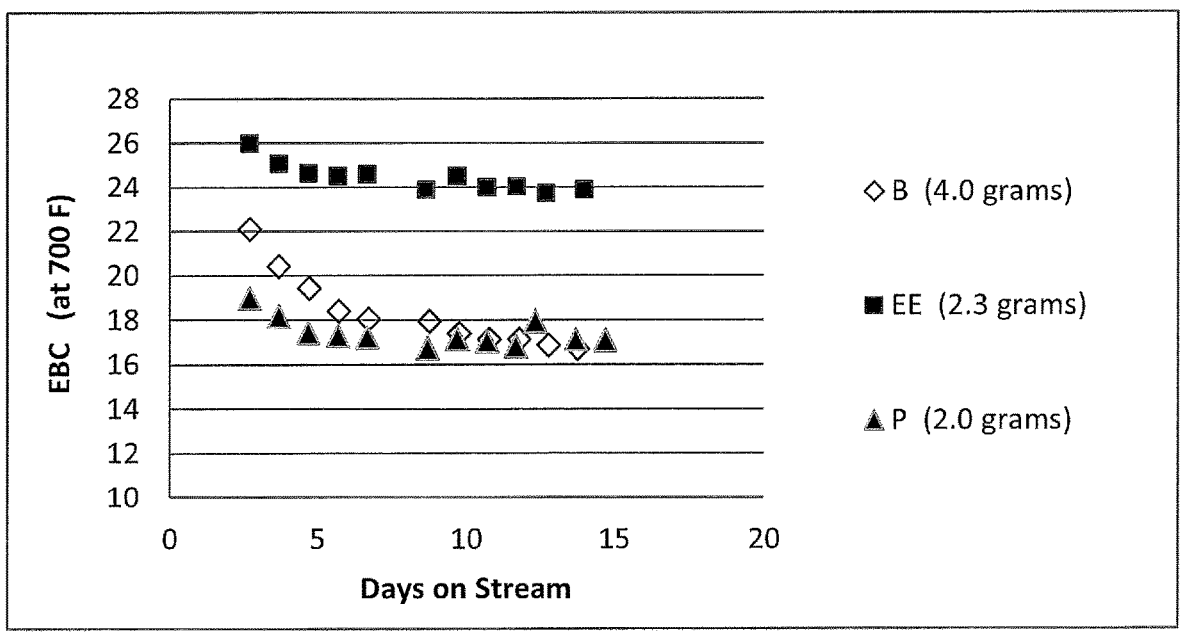
FIG. 14b shows ethylbenzene conversion activity versus days on stream of Catalysts B, EE and P.

FIGS. 14a and 14b shows the xylene isomerization and EB conversion activities for catalysts B, EE, and P. Both of the Mo-Desilicated ZSM-5 catalysts, EE and P, showed lower deactivation rates than the Catalyst B. After two weeks on stream the 4% Mo-Desilicated ZSM-5 catalyst (2.0-g loading) was a little less active for isomerization than the Catalyst B (4.0-g loading) but similar in EB conversion activity.

TABLE IX

Comparative Examples

| Sample | ICP Al wt % | ICP SAR | N$_2$ Ads Meso-pore S.A. m$^2$/g | Catalytic Rel. XIA | Catalytic XL/XIA | Catalytic EBC |
|---|---|---|---|---|---|---|
| KK | 1.72 | 50 | 259 | 1.00 | 1.00 | 40-42% |
| Zeolyst CBV 8014 | 1.06 | 83 | 170 | 0.28 | 1.93 | 31% |
| Comparative Example No. 1* | 1.32 | 66 | 207 | 0.37 | 1.42 | 29% |
| Comparative Example No. 2* | 1.29 | 68 | 204 | 0.35 | 1.39 | 29% |

*Comparative examples made as per "sample HW" in Chem. Eur. J. 2010, 16, 6224-6233

Comparative example catalysts were duplicated (1 and 2) to test reproducibility. The parent ZSM-5 for the comparative examples was Zeolyst CBV 8014 as per the referenced journal article. The parent ZSM-5 was analyzed and tested after calcination at 550 deg C. For the catalytic results desilicated ZSM-5 catalyst KK was used as a reference.

The Comparative catalysts were much less active for both xylene isomerization (XIA) and ethylbenzene conversion than KK. Also, their selectivity was worse than KK as indicated by higher XL/XIA ratio than KK. Per the journal article the crystal size of the comparative example parent ZSM-5 is less than 1 micron but has high SAR of approximately 80 to 83 as measured using ICP.

What is claimed is:

1. A method of making a xylene isomerization catalyst comprising the steps of:
   (i) contacting a ZSM-5 zeolite starting material having a silica to alumina molar ratio of about 20 to about 50, in the form of a powder having a mesopore surface area in the range of about 50 m$^2$/gram to about 200 m$^2$/gram in a reactor with a base at a temperature of about 20° C. to about 100° C. for a caustic treatment period of about 1 minute to about 10 hours to provide an intermediate zeolite material, wherein the ZSM-5 zeolite is present in the base in an amount of about 1 weight % to about 20 weight %, wherein the base is selected from the group consisting of:
   NaOH, LiOH, KOH, RbOH, CsOH, Mg(OH)$_2$, Ca(OH)$_2$, NH$_4$OH, Li$_2$O, Na$_2$O, K$_2$O, Rb$_2$O, Cs$_2$O, MgO, and CaO; or
   alkali metal alkoxides having the formula R'OM wherein R' is selected from the group consisting of methyl, ethyl, propyl, isopropyl, butyl, pentyl, and phenyl, and M is selected from the group consisting of Li, Na, and K; or
   alkyl ammonium hydroxides having the formula R"NH$_3$OH, R"$_2$NH$_2$OH, R"$_3$NHOH, R"$_4$NOH, wherein R" is selected from the group consisting of methyl, ethyl, propyl, isopropyl, and butyl; or
   any combination thereof;
   and wherein the base is added to the reactor incrementally or continuously during the caustic treatment period;
   (ii) recovering the intermediate ZSM-5 zeolite material of step (i);
   (iii) contacting the intermediate zeolite material with an acid at a temperature of about 20° C. to about 100° C. for an acid treatment period of about 1 minute to about 10 hours to provide an acid treated ZSM-5 zeolite product;
   (iv) recovering the acid treated ZSM-5 zeolite material; and
   (v) calcining the acid treated ZSM-5 zeolite material at a temperature in the range of about 300° C. to about 700° C. for a period of time in the range of about 0.2 hours to about 6 hours to provide a desilicated ZSM-5 zeolite product having a silica to alumina molar ratio of about 20 to about 150 and having a mesopore surface area greater than the mesopore surface area of the zeolite starting material and in the range of about 100 m²/gram to about 400 m²/gram.

2. The method of claim 1 wherein the ZSM-5 zeolite starting material has an average crystal length, width and thickness of less than 1 micron.

3. The method of claim 1 wherein the acid is selected from the group consisting of HF, HCl, HBr, HI, $HNO_2$, $HNO_3$, $H_2SO_3$, $H_2SO_4$, $H_3PO_3$, $H_3PO_4$, $H_3BO_3$, oxalic acid, citric acid, acetic acid, benzoic acid, formic acid, propionic acid, fluoroacetic acid, trifluoroacetic acid, lactic acid, tartaric acid, ascorbic acid, malonic acid, maleic acid, succinic acid, glutaric acid, adipic acid, 2-hydroxybenzoic acid, 3-hydoxybenzoic acid, and 4-hydoxybenzoic acid, or any combination thereof.

4. The method of claim 1, comprising the steps of:
(i) contacting a ZSM-5 zeolite starting material having a silica to alumina molar ratio of about 25 to about 50, in the form of a powder having a mesopore surface area in the range of about 90 m²/gram to about 150 m²/gram in a reactor with NaOH at a temperature of about 70° C. to about 90° C. for a caustic treatment period of about 30 minutes to about 120 minutes to provide an intermediate zeolite material, wherein the base is added to the reactor incrementally or continuously during the caustic treatment period;
(ii) recovering the intermediate ZSM-5 zeolite material of step (i);
(iii) contacting the intermediate zeolite material with oxalic acid at a temperature of about 20° C. to about 90° C. for an acid treatment period of about 60 minutes to about 300 minutes to provide an acid treated ZSM-5 zeolite product;
(iv) recovering the acid treated ZSM-5 zeolite material; and
(v) calcining the acid treated ZSM-5 zeolite material at a temperature in the range of about 400° C. to about 600° C. for a period of time in the range of about 2 hours to about 6 hours to provide a desilicated ZSM-5 zeolite product having a silica to alumina molar ratio of about 30 to about 80 and having a mesopore surface area greater than the mesopore surface area of the zeolite starting material and in the range of about 150 m²/gram to about 300 m²/gram.

5. The method of claim 4, wherein the incremental addition comprises adding four or more doses of base to the reactor at intervals of 15-30 minutes.

6. The method of claim 5, wherein each dose comprises about 50 weight % base.

7. The method of claim 1, wherein the desilicated ZSM-5 zeolite product has a silica to alumina molar ratio greater than the silica to alumina molar ratio of the zeolite starting material.

* * * * *